United States Patent [19]

Leboul et al.

[11] Patent Number: 5,716,994

[45] Date of Patent: Feb. 10, 1998

[54] ANTITUMOR AND ANTILEUKAEMIC SUBSTANCES, THEIR PREPARATION AND PHARMACEUTICAL COMPOSITIONS CONTAINING THEM

[75] Inventors: Jean Leboul, Gometz-la-ville; Jean Provost, Monts, both of France

[73] Assignee: Rhone-Poulenc Rorer S.A., Antony, France

[21] Appl. No.: 750,838

[22] PCT Filed: Jun. 20, 1995

[86] PCT No.: PCT/FR95/00814

§ 371 Date: Dec. 19, 1996

§ 102(e) Date: Dec. 19, 1996

[87] PCT Pub. No.: WO96/00205

PCT Pub. Date: Jan. 4, 1996

[30] Foreign Application Priority Data

Jun. 23, 1994 [FR] France .................... 94 07701
Jan. 9, 1995 [FR] France .................... 95 00160

[51] Int. Cl.$^6$ .................................................. A61K 31/12
[52] U.S. Cl. .......................... 514/680; 514/719; 568/327; 568/633
[58] Field of Search .................... 568/327, 633; 514/680, 719

[56] References Cited

U.S. PATENT DOCUMENTS 4,882,439  11/1989  Jones ........................... 568/327

*Primary Examiner*—James H. Reamer
*Attorney, Agent, or Firm*—Finnegan, Henderson, Farabow, Garrett & Dunner, L.L.P.

[57] ABSTRACT

(3-hydroxy-4-methoxybenzyl)-7-methylene-1-vinyl-2,3,3a,4,7,7a-hexahydroinden-4-one of formula (I):

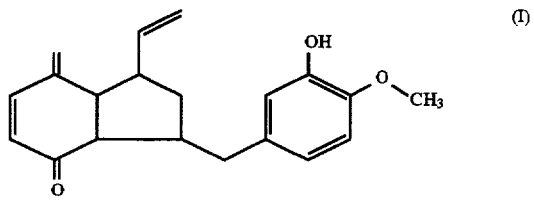

and 3-(3-hydroxy-4-methoxybenzyl)-4-hydroxy-7-methyl-1-vinylindan of formula (II):

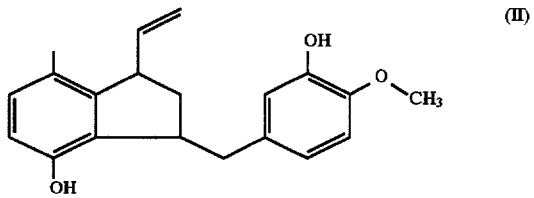

as well as their stereoisomeric forms are disclosed. Also disclosed are a process for producing these compounds from the plant *Ottelia alismoides* and pharmaceutical compositions containing them. The novel compounds of formulas (I) and (II) have remarkable antitumor and antileukaemic properties.

6 Claims, No Drawings

ANTITUMOR AND ANTILEUKAEMIC SUBSTANCES, THEIR PREPARATION AND PHARMACEUTICAL COMPOSITIONS CONTAINING THEM

The present invention relates to 3-(3-hydroxy-4-methoxybenzyl)-7-methylene-1-vinyl-2,3,3a,4,7,7a-hexahydroinden-4-one of formula (I):

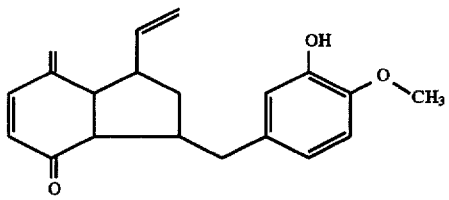

and 3-(3-hydroxy-4-methoxybenzyl)-4-hydroxy-7-methyl-1-vinylindan of formula (II):

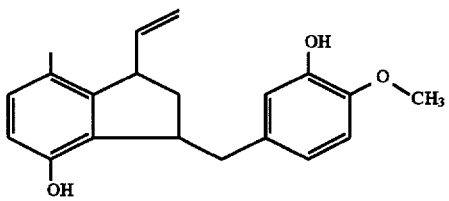

as well as their stereoisomeric forms, the process for producing them from the plant *Ottelia alismoides* and pharmaceutical compositions containing them.

More particularly, the present invention relates to the product of formula (I) which has the following characteristics:

specific rotation:

$[\alpha]^{20}$ (Na 589)=−20.8±1.0 (dichloromethane, c=0.5)

$[\alpha]^{20}$(Hg 436)=−32 ±1.2 (dichloromethane, c=0.5)

infrared spectrum:

main characteristic absorption bands at 3400, 3070, 2925, 2840, 1660, 1580, 1500, 1435, 1270, 1125 and 1025 $cm^{-1}$.

mass spectrum (DCI $NH_3$):328 $(M+NH_4)^+$ (EI):311 $(M+NH_4=OH)^+$ proton nuclear magnetic resonance spectrum (600 MHz; $CDCl_3$; δ in ppm):

6.99 (d, J=9 Hz, 1H); 6.80 (d, J=2 Hz, 1H); 6.77 (d, J=8 Hz, 1H), 6.69 (dd, J=2 and 8 Hz, 1H); 5.94 (d, J=9 Hz, 1H); 5.78 (m, 1H); 5053 (s, 1H); 5.32 (m, 2H); 4.98 (d, J=10 Hz, 1H); 4.95 (d, J=17 Hz, 1H); 3.88 (s, 3H); 3.07 (m, 1H); 2.88 (dd, J=6 and 8 Hz, 1H); 2.80 (t, J=8 and 8 Hz, 1H); 2.62 (m, 1H); 2.51 (m, 2H); 1.74 (m, 1H); 1.58 (m, 1H).

More particularly, the present invention relates to the product of formula (II) which has the following characteristics:

specific rotation:

$[\alpha]^\circ$(Na 589)=+32.3 ±1.3 (dichloromethane; c=0.5)

$[\alpha]^\circ$(Hg 436)=+75.0 ±1.8 (dichloromethane; c=0.5)

infrared spectrum:

main characteristic absorption bands at 3419, 3074, 1635, 1592, 1495, 1271, 1126 and 1029 $cm^{-1}$.

mass spectrum (DCI $NH_3$): 328 $(M+NH_4)^+$ (EI): 310 $(M)^+$ proton nuclear magnetic resonance spectrum (600 MHz; $CDCl_3$; δ in ppm;

coupling constant J in Hz): 1.95 (m, 1H); 2.05 (m, 1H); 2.18 (s, 3H); 2.62 (d, J=8 and 13, 1H0; 3.16 (dd, J=6 and 13, 1H); 3.58 (m, 1H); 3.83 (m, 1H); 3.88 (m, 1H); 4.25 (s, 1H); 4.98 (d, J=8, 1H); 5.01 (d, J=16, 1H); 5.58 (s, 1H); 5.78 (dd, J=8 and 16, 1H); 6.53 (d, J=7, 1H); 6.69 (dd, J=7 and 1, 1H); 6.79 (d, J=7, 1H); 6.82 (dd, J=1, 1H); 6.85 (d, J=7, 1H)

ultraviolet spectrum:

λ max=282 nm (ε=4650); 225 nm (shoulder); 207 (ε=48800) (c=10.1 $g/cm^3$; methanol)

λ max=282 nm; 225 nm (shoulder); 206 nm (c=10.1 $mg/cm^3$; methanol-hydrochloric acid)

λ max=297 nm (shoulder); 288 nm; 243 nm (shoulder); 214 nm (c=10.1 $mg/cm^3$; methanol-potassium hydroxide)

3-(3-Hydroxy-4-methoxybenzyl)-7-methylene-1-vinyl-2,3,3a,4,7,7a-hexahydroinden-4-one and 3-(3-hydroxy-4-methoxybenzyl)-4-hydroxy-7-methyl-1-vinylindan can be obtained from the plant *Ottelia alismoides* by extraction by means of a suitable solvent followed by the separation of the 3-(3-hydroxy-4-methoxybenzyl)-7-methylene-1-vinyl-2,3,3a,4,7,7a-hexahydroinden-4-one or of the 3-(3-hydroxy-4-methoxybenzyl)-4-hydroxy-7-methyl-1-vinylindan from the extract obtained.

*Ottelia alismoides*, which belongs to the Hydrocharitaceae family, is a submerged or partially floating aquatic plant. *Ottelia alismoides* has radical leaves which form, for the immersed part, a shrunken crown. The long floating part is petiolate, oval and lanceolate, oblong or cordate. The flowers are hermaphrodites and solitary, sessile with a long pedunculate spathe, and consist of three linear and oblong sepals and three large ovoid or orbicular petals.

According to the invention, *Ottelia alismoides*, in the form of the whole plant, generally dried and finely ground, is treated once or several times with a solvent chosen from aliphatic alcohols containing 1 to 4 carbon atoms and the aliphatic esters containing 1 to 6 carbon atoms to give, after concentration, a dry extract which is taken up in an aliphatic hydrocarbon containing 5 to 8 carbon atoms or a cycloaliphatic hydrocarbon containing 5 to 7 carbon atoms in order to obtain a solution from which the insoluble matter is separated by filtration and which, after concentration, gives a dry extract from which 3-(3-hydroxy-4-methoxybenzyl)-7-methylene-1-vinyl-2,3,3a,4,7,7a-hexahydroinden-4-one or 3-(3-hydroxy-4-methoxybenzyl)-4-hydroxy-7-methyl-1-vinylindan is separated by applying chromatographic techniques.

For the implementation of the process according to the invention for the production of the product of formula (I), it is particularly advantageous to carry out the extraction of the whole plant by means of ethanol and to treat the dry extract obtained with an aliphatic hydrocarbon such as hexane.

For the implementation of the process according to the invention for the production of the product of formula (II), it is particularly advantageous to carry out the extraction of the whole plant by means of methyl tert-butyl ether and to treat the dry extract obtained with an aliphatic hydrocarbon such as heptane combined with a nitrile such as acetonitrile.

The separation of 3-(3-hydroxy-4-methoxybenzyl)-7-methylene-1-vinyl-2,3,3a,4,7,7a-hexahydroinden-4-one or of 3-(3-hydroxy-4-methoxybenzyl)-4-hydroxy-7-methyl-1-vinylindan from the extract derived from the treatment with an aliphatic hydrocarbon optionally combined with a nitrile is generally carried out by high-performance liquid chromatography or by centrifugal partition chromatography.

3-(3-Hydroxy-4-methoxybenzyl)-7-methylene-1-vinyl-2,3,3a,4,7,7a-hexahydroinden-4-one and 3-(3-hydroxy-4-methoxybenzyl)-4-hydroxy-7-methyl-1-vinylindan have remarkable biological properties.

In vitro, 3-(3-hydroxy-4-methoxybenzyl)-7-methylene-1-vinyl-2,3,3a,4,7,7a-hexahydroinden-4-one and 3-(3-hydroxy-4-methoxybenzyl)-4-hydroxy-7-methyl-1-vinylindan exhibit the property of inhibiting the polymerization of tubulin.

Tubulin, derived from pig brain, is purified by three cycles of polymerization-depolymerization according to the method of M. L. SHELANSKI et al., Proc. Natl. Acad. Sci. USA, 70, 765–768 (1973) followed by chromatography on phosphocellulose according to the method of M. D. WEINGARTEN et al., Proc. Natl. Acad. Sci. USA, 72, 1858–1862 (1975).

Tubulin, at a concentration of 8.5 µM in 0.05M Mes buffer (pH=6.8), 0.25 mM $MgCl_2$, 0.5 mM EGTA, 3.4M glycerol and 1 mM GTP, is polymerized at 37° C. for 30 minutes after addition of $MgCl_2$ (6 mM) and increasing concentrations, from 0.8 to 16 µM, of 3-(3-hydroxy4-methoxybenzyl)-7-methylene-1-vinyl-2,3,3a,4,7,7a-hexahydroinden-4-one or 3-(3-hydroxy-4-methoxybenzyl)-4-hydroxy-7-methyl-1-vinylindan in solution at 1 mg/$cm^3$ in absolute ethanol.

The assembly of tubulin into microtubules results in an increase in the turbidity observed at 350 nm with the aid of spectrophotometer.

3-(3-Hydroxy-4-methoxybenzyl)-7-methylene-1-vinyl-2-3,3a,4,7,7a-hexahydroinden-4-one and 3-(3-hydroxy-4-methoxybenzyl)-4-hydroxy-7-methyl-1-vinylindan cause an inhibition of the polymerization of tubulin which results in an increase in the latent period, a decrease in the rate of polymerization as well as a lower turbidity in the stationary state. The concentration of the product of formula (I) which inhibits by 50% the polymerization of tubulin has a concentration of less than 5 NM and even of less than 1 NM for 3-(3-hydroxy-4-methoxybenzyl)-7-methylene-1-vinyl-2,3,3a,4,7,7a-hexahydroinden-4-one.

In vitro, 3-(3-hydroxy-4-methoxybenzyl)-7-methylene-1-vinyl-2,3,3a,4,7,7a-hexahydroinden-4-one and 3-(3-hydroxy-4-methoxybenzyl)-4-hydroxy-7-methyl-1-vinylindan manifest a cytotoxicity of less than 1 µg/$cm^3$ on the murine leukaemia cell lines P388, as well as on the resistant lines P388/DOX and even of less than 1 ng/$cm^3$ for 3-(3-hydroxy-4-methoxybenzyl)-7-methylene-1-vinyl-2,3,3a,4,7,7a-hexahydroinden-4-one.

The following examples illustrate the present invention.

EXAMPLE 1

8.8 kg of *Ottelia alismoides* in the form of the whole plant, dried and finely ground, are stirred in a monoplate filter equipped with a Tergal® fabric with 60 liters of 99.9% ethanol, denatured with cyclohexane, for 1 hour. After filtration under a nitrogen pressure of 2 bar, the plant is again extracted with 60 liters of ethanol for 1 hour, and then with 30 liters of ethanol for 12 hours. The plant is then washed with 30 liters of ethanol.

The ethanolic solution thus obtained is concentrated to a volume of 15 liters in a thermosyphon evaporator, and then concentrated to dryness under reduced pressure at 40° C.

80 g of soft green extract are thus obtained, which extract is taken up in 3 liters of hexane. After filtration of an insoluble matter (7 g), the filtrate is concentrated to dryness. 73 g of a product (extract A) are thus obtained whose inhibitory activity on the polymerization of tubulin ($IC_{50}$) is 75 µg/$cm^3$.

9.4 g of extract A are taken up in 200 $cm^3$ of cyclohexane. After filtration of an inactive insoluble matter (2 g), the cyclohexane-containing solution is loaded onto a column with 200 g of Merck silica (0.040–0.063 mm) for which the diameter/height ratio is equal to 15. The elution is performed with a cyclohexane-dichloromethane mixture with a gradient increasing by 5% dichloromethane, collecting 500 $cm^3$ fractions. The fractions which correspond to elution with the cyclohexane-dichloromethane mixtures 45–55, 40–60 and 35–65 by volume are combined and concentrated to dryness under reduced pressure at a temperature of close to 20° C. 1.2 g of a product are thus obtained whose activity is 2.5 µg/$cm^3$.

The product thus obtained is taken up in 5 $cm^3$ of a dichloromethane-methanol mixture (99-1 by volume) and chromatographed on a column with 50 g of Merck 60H silica, for which the diameter/height ratio is equal to 15, prepared with the same solvent. The elution is performed with a dichloromethane-methanol mixture (99-1 by volume), collecting 2 $cm^3$ fractions. The fractions 41 to 68 are combined and concentrated to dryness under reduced pressure. 70 mg of a product are thus obtained whose activity is 1 µg/$cm^3$, which product is purified by high-performance liquid chromatography on a BIORAD C18 HL-90-10 column, eluting with an acetonitrile-water mixture at a flow rate of 3 $cm^3$/minute and performing the detection by UV absorption at 254 nm. The collecting of the peak corresponding to the 19-minute retention peak provides 14 mg of pure 3-(3-hydroxy-4-methoxybenzyl)-7-methylene-1-vinyl-2,3,4a ,4,7,7a-hexahydroinden-4-one in the form of a pale yellow semisolid whose characteristics are the following:

specific rotation:

$[\alpha]°$(Na 589)=−20.8±1.0 (dichloromethane; c=0.5)

$[\alpha]°$(Hg 436)=32 ±1.2 (dichloromethane; c=0.5)

infrared spectrum:

main characteristic absorption bands at 3400, 3070, 2925, 2840, 1660, 1580, 1500, 1435, 1270, 1125 and 1025 $cm^{-1}$.

mass spectrum (DCI $NH_3$): 328 $(M+NH_4)^+$ (EI): 311 $(M+NH_4-OH)^+$ proton nuclear magnetic resonance spectrum (600 MHz; $CDCl_3$; δ in ppm):

6.99 (d, J=9 Hz, 1H); 6.80 (d, J=2 Hz, 1H); 6.77 (d, J=8 Hz, 1H), 6.69 (dd, J=2 and 8 Hz, 1H); 5.94 (d, J=9 Hz, 1H); 5.78 (m, 1H); 5053 (s, 1H); 5.32 (m, 2H); 4.98 (d, J=10 Hz, 1H); 4.95 (d, J=17 Hz, 1H); 3.88 (s, 3H); 3.07 (m, 1H); 2.88 (dd, J=6 and 8 Hz, 1H); 2.80 (t, J=8 and 8 Hz, 1H); 2.62 (m, 1H); 2.51 (m, 2H); 1.74 (m, 1H); 1.58 (m, 1H).

The product obtained can be visualized by thin-layer chromatography on Merck F254 silica, eluting with a dichloromethane-methanol mixture (99-1 by volume), and developing, after heating the plate at 100° C., with ceric sulphate at 0.1% in ethanol. The product appears in the form of a spot of Rf=0.5 with a violet-red colour.

EXAMPLE 2

2 g of extract A obtained in example 1 are taken up in 10 $cm^3$ of an ethyl acetate-heptane-methanol-water mixture (1-2-2-1 by volume) and then chromatographed by counter-current partition chromatography in a CPC SANKI apparatus having a 245 $cm^3$ column, the procedure being carried out under the following conditions:

| | |
|---|---|
| stationary phase: | heavy phase |
| mobile phase: | light phase |
| direction: | ascending |
| speed of rotation: | 1000 revolutions/minute |
| flow rate: | 3 cm³/minute |
| retention: | 80% |
| reversal of the direction: | at 170 minutes |

The injection is performed at equilibrium of the 2 phases. The fractions are collected every 2 minutes. Thin-layer-chromatography and the assay show that fractions 56 to 85 contain (3-hydroxy-4-methoxybenzyl)-7-methylene-1-vinyl-2,3,3a,4,7,7a-hexahydroinden-4-one. Purification of the product obtained by HPLC under the conditions described in Example 1 gives 2 mg of pure 3-(3-hydroxy-4-methoxybenzyl)-7-methylene-1-vinyl-2,3,3a,4,7,7a-hexahydroinden-4-one.

EXAMPLE 3

5 85 kg of *Ottelia alismoides* in the form of the whole plant, dried and finely ground, are stirred in a monoplate filter equipped with a Tergal® fabric with 400 liters of methyl tert-butyl ether for 1 hour and then left in contact for 12 hours. After filtration under a nitrogen pressure of 2 bar, the plant is again extracted with 400 liters of methyl tert-butyl ether for 1 hour and left in contact for 12 hours. The plant is then washed with 200 liters of methyl tert-butyl ether.

The ethereal solution thus obtained is concentrated to a volume of 15 liters in a thermosyphon evaporator, and then concentrated to dryness under reduced pressure at 40° C.

754 g of soft green extract are thus obtained, which extract is taken up in 30 liters of a heptane-acetonitrile mixture (1-1 by volume). After filtration of an inactive insoluble matter, the filtrate is concentrated to dryness. 270 g of an oily green-chestnut coloured product are thus obtained.

10 g of the extract obtained are taken up in 150 cm³ of an ethyl acetate-heptane-methanol-water mixture (2-3-3-2 by volume) and then chromatographed by counter-current partition chromatography in an ITO® type SFCC 800 apparatus having a volume of 2500 cm³ distributed in 3 cartridges, the procedure being carried out under the following conditions:

| | |
|---|---|
| stationary phase: | heavy phase |
| mobile phase: | light phase |
| mode: | ascending |
| speed of rotation: | 380 revolutions/minute |
| flow rate: | 8 cm³/minute |
| retention: | 46% |

The injection is performed with the 2 phases at equilibrium. The fractions are collected every 8 minutes. The separation is stopped after recovering 30 fractions. Fractions 19 to 26 are combined and concentrated to dryness. 3.5 g of an oily extract are thus obtained from which pure 3-(3-hydroxy-4-methoxybenzyl)-4-hydroxy-7-methyl-1-vinylindan is separated by chromatography on an AMICON silica column (0.030–0.070 mm) 3 cm in height and 1.2 cm in diameter. Elution is performed with heptane using an increasing methyl tert-butyl ether gradient and collecting 5 cm³ fractions. Fractions 22 and 23, which correspond to the elution with a heptane-methyl tert-butyl ether mixture (8-2 by volume), are combined and concentrated to dryness under reduced pressure. 0.5 mg of 3-(3-hydroxy-4-methoxybenzyl)-4-hydroxy-7-methyl-1-vinylindan is thus obtained in the form of a pale yellow solid whose characteristics are the following:

specific rotation:

$[\alpha]°(Na\ 589) = +32.3 \pm 1.3$ (dichloromethane; c=0.5)

$[\alpha]°(Hg\ 436) = +75.0 \pm 1.8$ (dichloromethane; c=0.5)

infrared spectrum:

main characteristic absorption bands at 3419, 3074, 1635, 1592, 1495, 1271, 1126 and 1029 cm$^{-1}$.

mass spectrum:

(DCI NH$_3$): 328 (M+NH$_4$)$^+$ (EI): 310 (M)$^+$ proton nuclear magnetic resonance spectrum (600 MHz; CDCl$_3$; δ in ppm; coupling constant J in Hz): 1.95 (m, 1H); 2.05 (m, 1H); 2.18 (s, 3H); 2.62 (d, J=8 F: and 13, 1H); 3.16 (dd, J=6 and 13, 1H); 3.58 (m, 1H); 3.83 (m, 1H); 3.88 (m, 1H); 4.25 (s, 1H); 4.98 (d, J=8, 1H); 5.01 (d, J=16, 1H); 5.58 (s, 1H); 5.78 (dd, J=8 and 16, 1H); 6.53 (d, J=7, 1H); 6.69 (dd, J=7 and 1, 1H); 6.79 (d, J=7, 1H); 6.82 (dd, J=1, 1H); 6.85 (d, J=7, 1H)

ultraviolet spectrum:

λ max=282 nm (ε=4650); 225 nm (shoulder); 207 (ε=48800) (c=10.1 g/cm³; methanol)

λ max=282 nm; 225 nm (shoulder); 206 nm (c=10.1 mg/cm³; methanol-hydrochloric acid)

λ max=297 nm (shoulder); 288 nm; 243 nm (shoulder); 214 nm (c=10.1 mg/cm³; methanol-potassium hydroxide)

The product obtained can be visualized by thin-layer chromatography on Merck F254 silica, eluting with a dichloromethane-methanol mixture (99-1 by volume) and developing with GIBBS reagent which is specific for phenols. The product appears in the form of a spot of Rf=0.48 with a blue colour.

3-(3-Hydroxy-4-methoxybenzyl)-7-methylene-1-vinyl-2,3,3a,4,7,7a-hexahydroinden-4-one and 3-(3-hydroxy-4-methoxybenzyl)-4-hydroxy-4-methyl-1-vinylindan manifest a significant inhibitory activity in relation to abnormal cell proliferation and possess therapeutic properties which allow the treatment of patients having pathological conditions associated with abnormal cell proliferation. The pathological conditions include abnormal cell proliferation of malignant or non-malignant cells of various tissues and/or organs, comprising, with no limitation being implied, muscular, bone or connective tissues, the skin, the brain, the lungs, the sex organs, the lymphatic or renal systems, the mammary or blood cells, the liver, the digestive system, the pancreas and the thyroid or adrenal glands. These pathological conditions may also include psoriasis, solid tumours, ovarian, breast, brain, prostate, colon or stomach cancer, cancer of the kidney or of the testicles, Kaposi's sarcoma, cholangiocarcinoma, choriocarcinoma, neuroblastoma, Wilms' tumour, Hodgkin's disease, melanomas, multiple myelomas, chronic lymphocytic leukaemia, acute or chronic granulocytic lymphomas. The new product according to the invention is particularly useful for the treatment of breast, ovarian or colon cancer or of cancer of the kidney. The product according to the invention can be used to prevent or delay the appearance or the reappearance of pathological conditions or to treat these pathological conditions.

The products according to the invention can be administered to a patient in different forms suitable for the chosen route of administration, which is preferably the parenteral route. Administration via the parenteral route comprises intravenous, intraperitoneal, intramuscular or subcutaneous administrations. More particularly preferred is the intraperitoneal or intravenous administration.

The present invention also comprises the pharmaceutical compositions which contain 3-(3-hydroxy-4-methoxybenzyl)-7-methylene-1-vinyl-2,3,3a,4,7,7a-hexahydroinden-4-one or 3-(3-hydroxy-4-methoxybenzyl)-4-hydroxy-7-methyl-1-vinylindan in a sufficient quantity suitable for use in human or veterinary therapy. The compositions can be prepared according to the usual methods using one or more pharmaceutically acceptable adjuvants, carriers or excipients. Suitable carriers include diluents, sterile aqueous media and various solvents which are non-toxic. Preferably, the compositions are provided in the form of aqueous solutions or suspensions, of injectable solutions which may contain emulsifying agents, colourings, preservatives or stabilizers.

The choice of adjuvants or excipients may be determined by the solubility and the chemical properties of the product, the specific mode of administration and good pharmaceutical practices.

For parenteral administration, aqueous or non-aqueous sterile solutions or suspensions are used. For the preparation of non-aqueous solutions or suspensions, there may be used natural vegetable oils such as olive oil, sesame oil or paraffin oil or injectable organic esters such as ethyl oleate. Aqueous solutions are suitable for intravenous administration in so far as the pH is appropriately adjusted and where isotonicity is achieved, for example, with a sufficient quantity of sodium chloride or glucose. The sterilization can be performed by heating or by any other means which does not impair the composition.

It is well understood that all the products entering into the compositions according to the invention must be pure and non-toxic for the quantities used.

The compositions may contain at least 0.001% of therapeutically active product. The quantity of active product in a composition is such that a suitable dosage can be prescribed. Preferably, the compositions are prepared such that a unit dose contains about 0.01 to 100 mg of active product for parenteral administration.

The therapeutic treatment can be carried out concurrently with other therapeutic treatments including antineoplastic drugs, monoclonal antibodies, immunological therapies or radiotherapies or biological response modifiers. Response modifiers include, with no limitation being implied, lymphokines, cytokines such as interleukins, interferons ($\alpha$, $\epsilon$ or $\delta$) and TNF. Other chemotherapeutic agents useful in the treatment of disorders due to the abnormal proliferation of cells include, with no limitation being implied, alkylating agents such as nitrogen mustards such as mechloretamine, cyclophosphamide, melphalan and chlorambucil, alkyl sulphonates such as busulphan, nitrosoureas such as carmustine, lomustine, semustine and streptozocine, triazenes such as dacarbazine, antimetabolites such as folic acid analogs such as methotrexate, pyrimidine analogs such as fluorouracil and cytarabine, purine analogs such as mercaptopurine and thioguanine, natural products such as alkaloids from vinca such as vinblastine, vincristine and vendesine, epipodophyllotoxins such as etoposide and teniposide, antibiotics such as dactinomycin, daunorubicin, doxorubicin, bleomycin, plicamycin and mitomycin, enzymes such as L-asparaginase, various agents such as platinum coordination complexes such as cisplatin, substituted ureas such as hydroxyurea, methylhydrazine derivatives such as procarbazine, adrenocorticol suppressors such as mitotane and aminoglutethymide, hormones and antagonists such as adrenocorticosteroids such as prednisone, progestines such as hydroxyprogesterone caproate, methoxyprogesterone acetate and megestrol acetate, oestrogens such as diethylstilbestrol and ethynylestradiol, antioestrogens such as tamoxifen, androgens such as testosterone propionate and fluoxymesterone.

The doses used for the implementation of the methods according to the invention are those which allow a prophylactic treatment or a maximum therapeutic response. The doses vary according to the form of administration and the characteristics specific to the subject to be treated. In general, the doses are those which are therapeutically effective for the treatment of disorders due to abnormal cell proliferation. The product according to the invention can be administered as often as necessary in order to obtain the desired therapeutic effect. Some patients may respond rapidly to relatively high or low doses and then require low or no maintenance doses. Generally, low doses will be used at the beginning of the treatment and, if necessary, increasingly high doses will be administered until an optimum effect is obtained. For other patients, it may be necessary to administer maintenance doses 1 to 8 times per day, preferably 1 to 4 times, depending on the physiological needs of the patient considered. It is also possible that for certain patients, it may be necessary to use only one to two daily administrations.

In man, using the intravenous route, the doses are generally between 0.05 and 50 mg/kg and, preferably, between 0.01 and 5 mg/kg and, still more specifically, between 0.1 and 2 mg/kg. It is understood that, in order to choose the most appropriate dosage, the administration route, the patient's weight, his general state of health, his age and all the factors which may influence the efficacy of the treatment should be taken into account.

The following example illustrates a composition according to the invention.

EXAMPLE 4

40 mg of the product obtained in Example 1 are dissolved in 1 cm³ of Emulphor EL 620 and 1 cm³ of ethanol, and then the solution is diluted by addition of 18 cm³ of physiological saline.

The composition is administered by infusion for 1 hour by introducing in physiological saline.

We claim:

1. A compound selected from 3-(3-hydroxy-4-methoxybenzyl)-7-methylene-1-vinyl-2,3,3a,4,7,7a-hexahydroinden-4-one of formula (I):

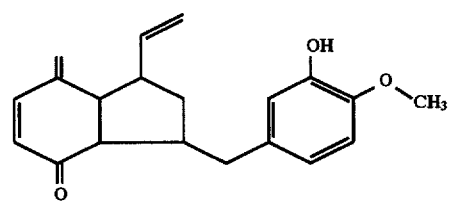

3-(3-hydroxy-4-methoxybenzyl)-4-hydroxy-7-methyl-1-vinylindan of formula (II):

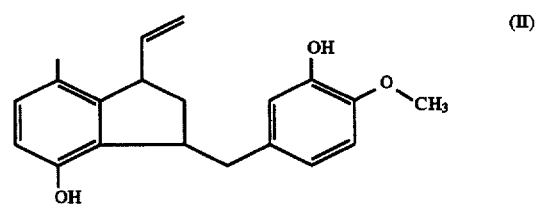

or a stereoisomer thereof.

2. A compound of formula (I) according to claim 1, wherein said compound has a specific rotation with the following values:

$[\alpha]^{20}$ (Na 589)=−20.8±1.0 (dichloromethane, c=0.5) and
$[\alpha]^{20}$ (Hg 436)=−32±1.2 (dichloromethane, c=0.5);

wherein said compound has an infrared spectrum with main characteristic absorption bands at 3400, 3070, 2925, 2840, 1660, 1580, 1500, 1435, 1270, and 1025 cm$^{-1}$;

wherein said compound has a mass spectrum with the following values:

(DCI NH$_3$): 328 (M+NH$_4$)$^+$ and (EI): 311 (M+NH$_4$=OH)$^+$; and wherein said compound has a proton nuclear magnetic resonance spectrum with the following values:(600 MHz; CDCl$_3$; δ in ppm): 6.99 (d, J=9 Hz, 1H); 6.80 (d, J=2 Hz, 1H); 6.77 (d, J=8 Hz, 1H), 6.69 (dd, J=2 and 8 Hz, 1H); 5.94 (d, J=9 Hz, 1H); 5.78 (m, 1H); 5053 (s, 1H); 5.32 (m, 2H); 4.98 (d, J=Hz, 1H); 4.95 (d, J=17 Hz, 1H); 3.88 (s, 3H); 3.07 (m, 1H); 2.88 (dd, J=6 and 8 Hz, 1H); 2.80 (t, J=8 and 8 Hz, 1H); 2.62 (m, 1H); 2.51 (m, 2H); 1.74 (m, 1H); 1.58 (m, 1H).

3. A compound of formula (II) according to claim 1, wherein said compound has a specific rotation with the following values:

$[\alpha]^{20}$(Na 589)=+32.3±1.3 (dichloromethane; c=0.5) and
$[\alpha]^{20}$(Hg 436)=+75.0±1.8 (dichloromethane; c=0.5);

wherein said compound has an infrared spectrum with main characteristic absorption bands at 3419, 3074, 1635, 1592, 1495, 1271, 1126 and 1029 cm$^{-1}$;

wherein said compound has a mass spectrum with the following values:

(DCI NH$_3$): 328 (M+NH$_4$)$^+$ and (EI: 310 (M)$^+$;

wherein said compound has a proton nuclear magnetic resonance spectrum with the following values: (600 MHz; CDCl$_3$; δ in ppm; coupling constant J in Hz): 1.95 (m, 1H); 2.05 (m, 1H); 2.18 (s, 3H); 2.62 (d, J=8 and 13, 1H); 3.16 (dd, J=6 and 13, 1H); 3.58 (m, 1H); 3.83 (m, 1H); 3.88 (m, 1H); 4.25 (s, 1H); 4.98 (d, J=8, 1H); 5.01 (d, J=16, 1H); 5.58 (s, 1H); 5.78 (dd, J=8 and 16, 1H); 6.53 (d, J=7, 1H); 6.69 (dd, J=7 and 1, 1H); 6.79 (d, J=7, 1H); 6.82 (dd, J=1, 1H); 6.85 (d, J=7, 1H); and wherein said compound has an ultraviolet spectrum with the following values:

λ max=282 nm (ε=4650); 225 nm (shoulder); 207 (ε=48800) (c=10.1 g/cm$^3$; methanol), λ max=282 nm; 225 nm (shoulder); 206 nm (c=10.1 mg/cm$^3$; methanol-hydrochloric acid), and λ max=297 nm (shoulder); 288 nm; 243 nm (shoulder); 214 nm (c=10.1 mg/cm$^3$; methanol-potassium hydroxide).

4. A process for the preparation of a product according to claim 1, said process comprising the steps of:

extracting the plant *Ottelia alismoides* by means of a suitable solvent, and separating the product according to claim 7 from the extract obtained.

5. A process according to claim 4, further comprising the steps of:

extracting said plant by means of a solvent selected from aliphatic alcohols containing 1 to 4 carbon atoms and aliphatic ethers containing 1 to 6 carbon atoms;

concentrating the extract obtained to give a dry extract;

taking up said dry extract with a solvent selected from aliphatic hydrocarbons containing 5 to 8 carbon atoms and cycloaliphatic hydrocarbons containing 5 to 7 carbon atoms, which may be combined with a nitrile containing 1 to 4 carbon atoms, to give a solution containing insoluble matter;

separating the insoluble matter from said solution;

concentrating the resulting solution to give an extract; and separating 3-(3-hydroxy-4-methoxybenzyl)-7-methylene-1-vinyl-2,3,3a,4,7,7a-hexahydroinden-4-one or 3-(3-hydroxy-4-methoxybenzyl)-4-hydroxy-7-methyl-1-vinylindan from said extract.

6. A pharmaceutical composition comprising a pharmaceutically effective amount of at least one compound according to claim 1, wherein said at least one compound is in the pure state or is combined with one or more pharmaceutically acceptable diluents or adjuvants and may further be combined with at least one therapeutically active product.

\* \* \* \* \*